United States Patent [19]

Hannan et al.

[11] Patent Number: 4,904,183
[45] Date of Patent: Feb. 27, 1990

[54] ORTHODONTIC DEBONDING METHOD AND TOOL

[75] Inventors: Clarence W. Hannan; Wilford A. Snead, both of San Dimas; Jirina V. Pospisil, Monrovia; Robert P. Eckert, Alta Loma, all of Calif.

[73] Assignee: Unitek Corporation, Monrovia, Calif.

[21] Appl. No.: 171,966

[22] Filed: Mar. 23, 1988

Related U.S. Application Data

[63] Continuation-in-part of Ser. No. 47,786, May 8, 1987, abandoned.

[51] Int. Cl.⁴ .............................................. A61C 7/00
[52] U.S. Cl. ...................................................... 433/3
[58] Field of Search ................................... 433/2, 3, 4

[56] References Cited

U.S. PATENT DOCUMENTS 2,602,998  7/1952  Sprague ............................... 433/141
4,553,932 11/1985  Armstrong et al. ..................... 433/4

Primary Examiner—Robert Peshock
Attorney, Agent, or Firm—Donald M. Sell; Walter N. Kirn; James D. Christoff

[57] ABSTRACT

Debonding of cemented orthodontic brackets from teeth by application of a quick twisting force to fracture the adhesive bond. A torquing tool has slotted ends making a close slip fit over mesial and distal side surfaces of the bracket, and has a flattened center section providing a good tactile sense of applied force. The method and tool are especially useful with brackets made of brittle ceramic material.

16 Claims, 4 Drawing Sheets

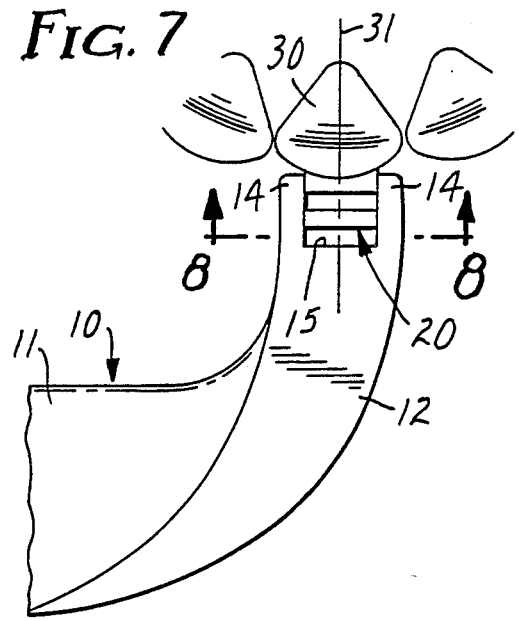
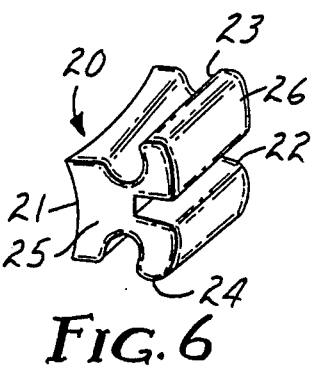
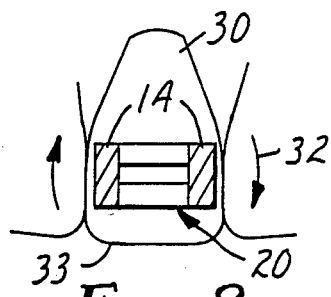
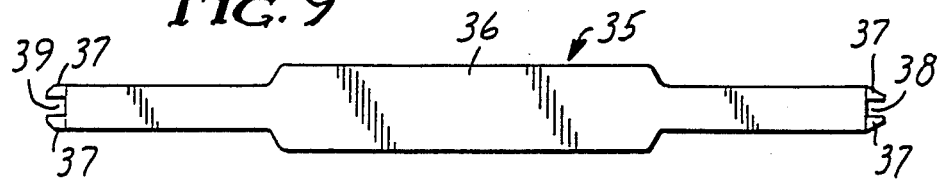
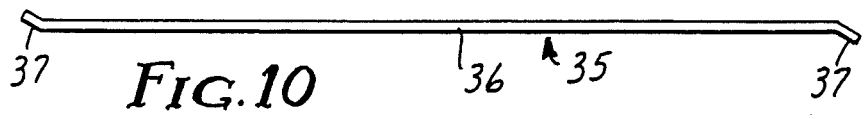
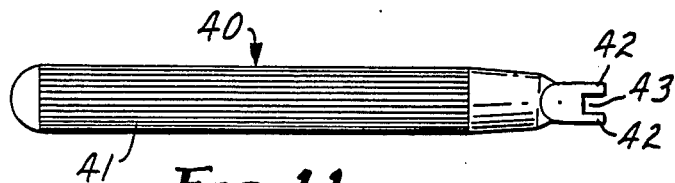
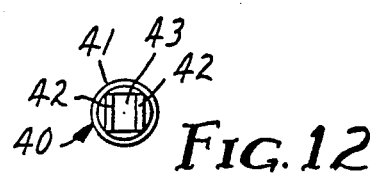

ORTHODONTIC DEBONDING METHOD AND TOOL

CROSS-REFERENCE TO RELATED APPLICATION

This is a continuation-in-part of U.S. Pat. Application 047,786 filed May 8, 1987 and now abandoned.

BACKGROUND OF THE INVENTION

Orthodontic brackets are appliances used in treatment programs to correct the alignment of improperly positioned teeth. Brackets are small slotted bodies, typically shaped to mate with the natural contour of the associated teeth, and slotted to receive an arch wire which delivers corrective force urging each malpositioned tooth toward proper alignment.

Secure attachment of brackets to teeth is accomplished in several ways. Traditionally, brackets have been made of metal, and welded to metal tooth bands contoured to fit snugly over the teeth for cemented attachment. This banded attachment continues to be widely used for back (molar) teeth where maximum bracket and attachment strength is desired, and the bands and brackets are not visible when the patient smiles.

A development of the last several decades is direct cemented attachment of a bracket to the tooth surface, and without use of a tooth band. Cemented or direct-bond brackets of this type have come into widespread use because elimination of the bands minimizes the size of the visible appliances on the teeth, and presents a more pleasing appearance when smiling.

Direct-bond brackets have been made of both metal and plastic but a recent advance is the construction of brackets from ceramic materials. Ceramic brackets are strong, and can be made almost invisible against the tooth surface by proper choice of materials. Bonding adhesives for ceramic brackets have become available, and provide a secure bracket attachment to the associated tooth. Ceramic brackets, however, are hard and brittle, and are more difficult to remove or debond from the teeth at the end of the treatment phase which requires brackets.

Bracket debonding involves breaking or fracturing the adhesive interface between tooth and bracket base to enable bracket removal, followed by cleaning of the tooth surface to remove any residual adhesive. Debonding of metal or plastic brackets (which are relatively ductile as compared to ceramic brackets) is usually done by breaking or shearing the adhesive bond with a plier-like debonding tool with chisel-like tips which peel the bracket away from the tooth.

Conventional debonding pliers and techniques have been found unsatisfactory for removal of ceramic brackets for several reasons. First, the high bond strength of the adhesive interface tends to resist conventional linear peeling forces. Second, the brittleness of ceramic brackets leads to bracket fracture and difficult removal with conventional debonding tools, especially when debonding force is applied to bracket tie wings which are structurally weaker than the main bracket body.

We have found that debonding of ceramic brackets is safely and effectively achieved by applying a quick rotary or twisting force to the bracket with a special tool designed to clasp the mesial and distal side surfaces of the bracket. This method and tool produce good fracturing of the adhesive bond with minimum risk of bracket breakage, and with no greater patient discomfort than experienced when removing a direct-bond metal or plastic bracket with a conventional debonding plier.

SUMMARY OF THE INVENTION

This invention relates to a method and tool for debonding a cemented orthodontic appliance such as a bracket from a tooth. In method terms, the invention comprises applying a close-fitting tool to opposed bracket surfaces, and applying a twisting force about an axis generally normal to the bracket base and tooth surface to fracture the adhesive bond. A tool for performing the method has a handle portion, and an end portion with a pair of spaced-apart tips defining therebetween a slot to receive the bracket. Preferably, the tool has a flattened and elongated center section with laterally and oppositely extending offset ends, each end being slotted to make a close slip fit over the bracket. The slots are preferably inwardly relieved to define at their outer ends an opposed pair of lands configured to engage only the strong base portion of the bracket.

BRIEF DESCRIPTION OF THE DRAWINGS

FIG. 6 is a pictorial view of a ceramic orthodontic bracket;

FIG. 7 is a generally vertical view of the tool as fitted over an orthodontic bracket on a tooth;

FIG. 8 is a generally horizontal sectional view of the tool and bracket on line 8—8 of FIG. 7;

FIGS. 9–10 are plan and side views of a first alternative embodiment of the tool;

FIGS. 11–12 are plan and side views of a second alternative embodiment of the tool;

DETAILED DESCRIPTION OF THE PREFERRED EMBODIMENTS

Figure 1:
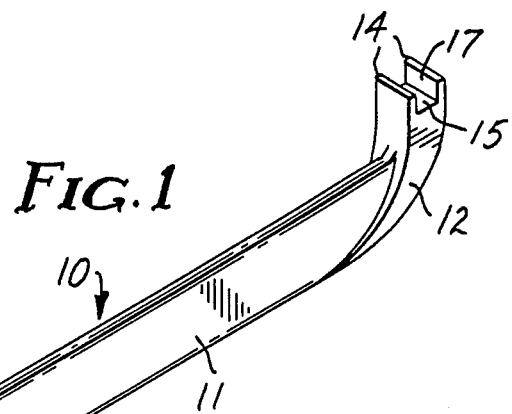
FIG. 1 is a pictorial view of a debonding tool according to the invention.
Figure 2:
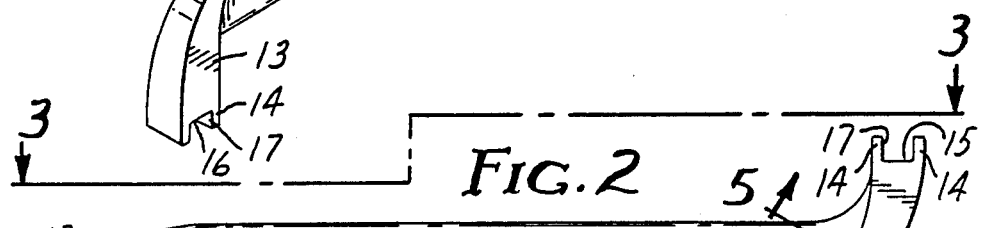
FIG. 2 is a plan view of the tool, the opposite side of the tool being similarly shaped.
Figure 3:
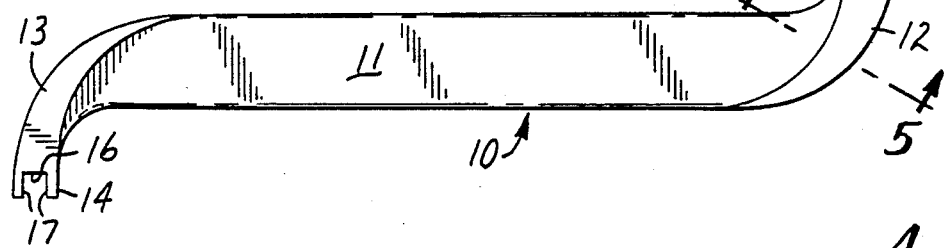
FIG. 3 is a side view on line 3—3 of FIG. 2.
Figure 4:
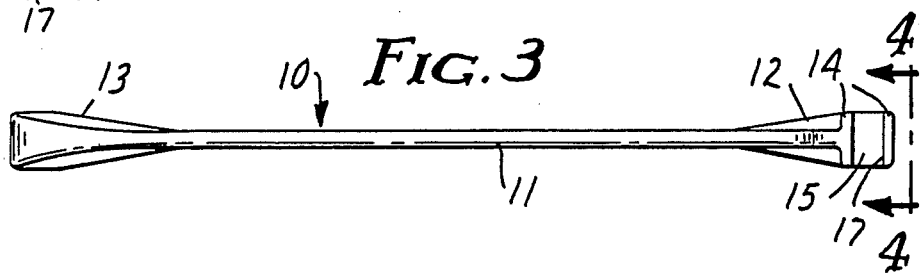
FIG. 4 is an end view on line 4—4 of FIG. 2.
Figure 5:
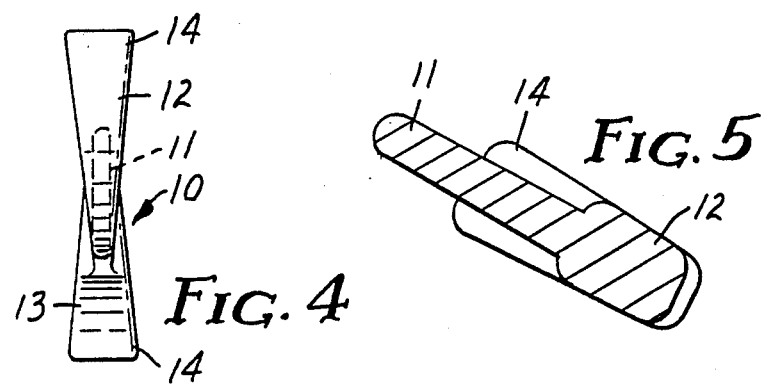
FIG. 5 is an enlarged section on line 5—5 of FIG. 2.

A presently preferred style of a debonding tool 10 according to the invention is shown in FIGS. 1–5. The tool has an elongated rectangular-cross-section shank or central portion 11 which provides a convenient surface for gripping the tool. A pair of oppositely oriented end portions 12 and 13 extend laterally from opposite ends of the central portion. The end portions are generally square or only slightly rectangular in cross-section, and are substantially larger in side dimension than the slender dimension of the central portion.

Each end portion terminates in a pair of spaced-apart beaks or tips 14, and the tips define therebetween a pair of rectangular slots 15 and 16 at opposite ends of the tool. The longitudinal axis of each slot, and hence inner sidewall surfaces 17 of tips 14, extend perpendicularly to the major plane of flattened central portion 11.

The double-ended tool is generally symmetrical, with the exception that slots 15 and 16 are of different widths to accommodate two different sizes of cemented orthodontic brackets. While the tool can be assembled from separate components, it is preferably an integral structure which is machined from a bar of stainless steel (Type 440 is satisfactory). After machining, the tips are hardened by conventional heat treating to resist scratching or abrasion when used with brackets made of hard ceramic materials.

In a typical configuration, the tool is about 4.25 inches in overall length, and the central handgrip portion is about 0.45 inch wide and 0.070 inch thick. The end portions are approximately one-fourth inch square in cross-section, and protrude laterally about 0.40 inch from the central portion. For styling purposes, the end portions are preferably smoothly curved and faired into the central portion as shown in the drawings, and this feature also makes the tool comfortable to hold and use.

Tool 10 is useful for debonding metal and plastic orthodontic brackets, but is especially adapted for removing hard and brittle ceramic brackets which cannot be easily and uniformly debonded with conventional plier-type tools. FIG. 6 shows a representative ceramic bracket 20 of a style useful on central and lateral maxillary incisor teeth.

Bracket 20 is an integrally formed body having a dished concave base 21 of compound curvature matching the somewhat convex labial or front surface of a tooth on which the bracket is to be bonded. A conventional rectangular archwire slot 22 extends rearwardly from the front surface of the bracket body, and upper and lower tie wings 23 and 24 provide an anchorage for a conventional ligature (not shown) which secures an archwire in the bracket slot.

The bracket body has generally flat and parallel mesial and distal side surfaces 25 and 26 which are spaced apart by the mesiodistal width of the bracket. The width of slots 15 and 16 of tool 10 are dimensioned to be a snug slip fit with two different bracket widths, placing inner sidewall surfaces 17 of the tool tips against bracket side surfaces 25 and 26 when the tool is fitted over the bracket. The slot widths are variable to mate with specific brackets, and widths of about 0.150 and 0.105 inch are typical for twin-wing and single-wing brackets respectively.

FIGS. 7 and 8 show bracket 20 as adhesively bonded to an incisor tooth 30 at the completion of the treatment phase which requires use of brackets. The usual archwire (not shown) has been removed in readiness for bracket removal, and tips 14 of the debonding tool fitted over the bracket side surfaces to seat the bracket body in tool slot 16.

To effect debonding, the orthodontist or assistant grasps central handle portion 11 of the tool, and rotates tips 14 in a quick snapping movement about an axis 31 (FIG. 7) generally perpendicular to the front surfaces of the bracket and underlying tooth. This rotary movement is suggested by arrows 32 in FIG. 8, and can be either clockwise or counterclockwise. Rapid twisting movement of the tool helps to provide an even distribution of forces during debonding.

Preferably, an occlusal edge 33 of tooth 30 is stabilized during bracket debonding by having the patient bite on a cotton roll placed between the adjacent occlusal edges of the upper and lower teeth. Alternatively, the orthodontist can firmly position a fingertip against the occlusal edge to minimize a reaction force in the tooth root during debonding tool rotation. Stabilization of the tooth, and quick rotary movement of the tool, combine to minimize patient discomfort which might otherwise arise from excessive compression of the periodontal ligament surrounding the tooth root.

The amount of torque required to debond a bracket will vary depending on the size of the bracket base, and the strength of the adhesive interface between the tooth and bracket base. This force may be in the range of several inch pounds, but an orthodontist quickly gains a sense of the proper force to apply.

If desired, the tool can be used initially on brackets bonded to artificial teeth in an arch model as a training exercise to build operator confidence and skill in the debonding technique. Use of a central tool portion 11 of slender and flat tab-like shape is preferred as it provides the orthodontist with a good "feel" or tactile sense of the applied lever-arm force, and clear sensing of adhesive fracture.

A subtle advantage of rotational debonding movement of the bracket with respect to the tooth arises from the compound and somewhat convex natural curvature of the tooth surface to which the bracket is secured, and the mating curvature of the bracket base. Twisting rotation of the bracket misaligns these mating surfaces, and lifts the bracket base from the tooth surface in a camming action. The onset of this movement initiates an adhesive fracture (by torsional shearing and tensile forces) which propagates through the adhesive interface to break the bond.

When the adhesive bond is broken, the bracket falls free from the tooth, and is usually retained in the debonding tool for convenient removal from the patient's mouth. Should the bracket drop from the tool upon debonding, it can still be easily removed from the mouth. Bracket removal is followed by conventional procedures for removing any residual adhesive from the tooth surface.

As mentioned above, the method and tool of this invention are useful in debonding of metal and plastic brackets and similar appliances, but the need for an improved tool and technique is an outgrowth of the recent development of ceramic brackets. In contrast to metal and plastic materials which are relatively resilient or ductile, ceramics are very hard and brittle, and somewhat unpredictable in tensile strength. These structural characteristics result in a significant risk of bracket fracture or shattering if conventional debonding tools are used with ceramic brackets.

When used with ceramic brackets, it is important to provide a close mating fit between the bracket and tool slots 15 or 16, and to avoid gripping the bracket on structurally weak surfaces. Typical commercially available ceramic brackets have essentially flat and parallel mesial and distal side surfaces 25 and 26, and tool tips 14 are accordingly flat and parallel, and spaced apart by the bracket width to fit snugly (preferably with no more than a few thousandths of an inch of overall clearance) against the bracket sides. The shape of the tool tips can of course be modified to mate with any other noncircular surface contour on the bracket.

Gripping of the mesial and distal sides of a ceramic bracket is also preferred, because it avoids application of debonding force to relatively thin tie wings 23 and 24 which pose a risk of fracture if the tool tips are positioned over the gingival and occlusal bracket surfaces. More generally, the concept is to apply the debonding torque to the structurally strongest parts of the bracket to minimize risk of bracket fracture.

Experience has shown that occasional ceramic-bracket breakage will occur, even with a close-fitting tool and proper technique. We have found that if breakage is sensed during tool rotation, further rotation should nevertheless be continued as there is a good probability that complete debonding will be achieved, and the bracket fragments will be largely contained in the tool slot.

Although tool 10 has been described in a preferred embodiment, other tool styles may be used as suggested in FIGS. 9-12. For example, a tool 35 of sheet-metal construction is shown in FIGS. 9-10, and has an enlarged handgrip central portion 36, and angled or offset tips 37 with slots 38 and 39 of two different widths to accommodate brackets of different widths. Another variation is a handle (not shown) with a gripping chuck to receive interchangeable blades of the shape of the ends of tool 35 on opposite sides of central portion 36.

FIGS. 11-12 show a machined tool 40 having a cylindrical handle 41 which conically tapers to a tip 42 with a bracket-receiving slot 43. Tool 40 can be made in a double-ended version if dual-slot capability is desired.

Figure 13A:
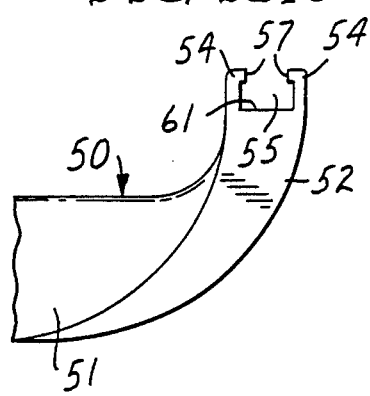
FIGS. 13A–B are top and front views respectively of one end of a tool generally similar to that shown in FIGS. 1–5, but with a modified bracket-receiving slot.
Figure 13B:
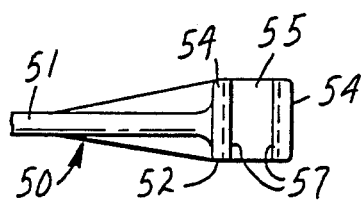

FIGS. 13A-B show one end of a tool 50 which is generally similar to tool 10, and is a presently preferred embodiment of the invention in that the possibility of debonding force being applied to relatively weaker bracket portions is minimized. In common with tool 10, tool 50 has a handgrip central portion 51 with an end portion 52 (the opposite end portion is not shown).

Figure 13C:
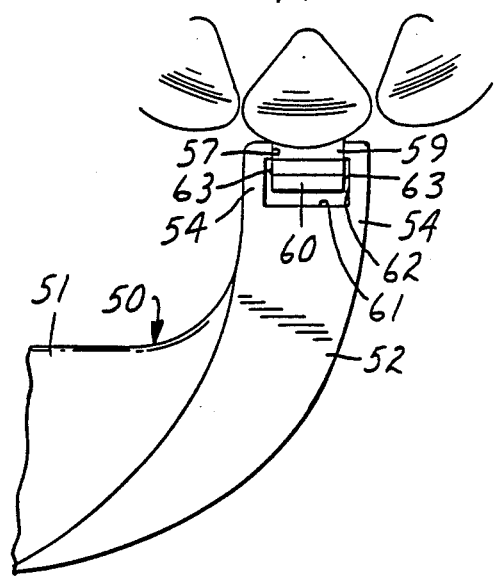
FIG. 13C is a view similar to FIG. 7, but showing the tool of FIGS. 13A–B.

End portion 52 terminates in a pair of beaks or tips 54 between which a slot 55 is defined. Tips 54 differ from tips 14 of tool 10 in that the inner surface of each tip 54 defines an inwardly extending projection or land 57. The entrance portion of slot 55 is thus narrowed by lands 57 which are spaced apart to make a slip fit over a base 59 of a bracket 60 as shown in FIG. 13C.

The portion of slot 55 which is between lands 57 and a slot base 61 is wider than bracket 60 to provide clearance spaces 62 (FIG. 13C) between the tool tips and mesial and distal side surfaces 63 of the tiewing portion of bracket 60. With this arrangement, torsional debonding force is applied by tool 50 only to the structurally strong base of the bracket, and the risk of fracturing the structurally weaker bracket tiewing portion is minimized.

Figure 14A:
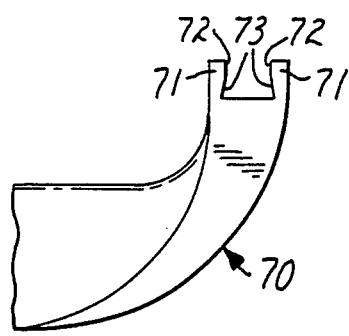
FIGS. 14A–B are top and side views respectively of an alternative embodiment of the tool shown in FIGS. 13A–B.
Figure 14B:
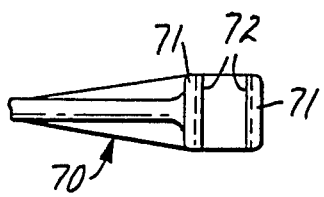
Figure 15A:
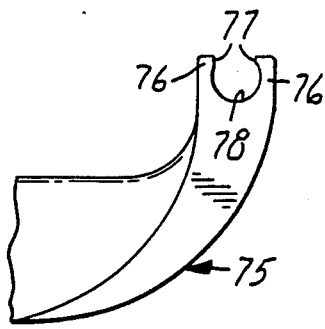
FIGS. 15A–B are top and side views respectively of a second alternative embodiment of the tool shown in FIGS. 13A–B.
Figure 15B:
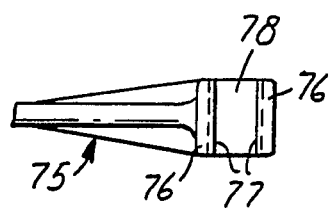

In the style of relieved-slot tool just described, the slot need not necessarily be rectangular, and a tool 70 is shown in FIGS. 14A-B with tips 71 having inwardly projecting lands 72 beneath which slot sidewalls 73 diverge outwardly to provide the desired clearance of the tips from the bracket tiewing side surfaces. Similarly, an alternative tool 75 is shown in FIGS. 15A-B with tips 76 having inwardly projecting lands 77 beneath which slot sidewalls 78 are arcuately shaped to provide the desired clearance spaces. In any of these embodiments, the relieved or enlarged inner portion of the slot beneath the tip lands is dimensioned to accept without contact the bracket tiewing portion which extends from the engaged bracket base.

Figure 16A:
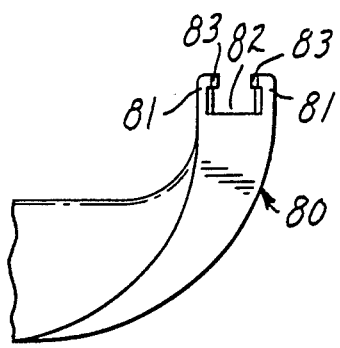
FIGS. 16A–B are top and side views respectively of a third alternative embodiment of the tool shown in FIGS. 13A–B.
Figure 16B:
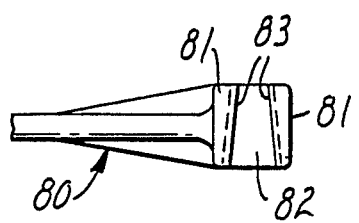

The concept of the invention is not limited to debonding of brackets with absolutely parallel mesial and distal base side surfaces, and a tool 80 is shown in FIGS. 16A-B which is useful with bracket bases which are tapered. Tool 80 is similar to those just described, with the exception that tips 81 define a tapered entrance slot 82 between base-gripping lands 83.

The primary present use of ceramic brackets is on the front (labial or buccal) surfaces of the incisor, cuspid and bicuspid teeth where the attractive and nearly invisible appearance of the ceramic material is desired by patients. The tools described above are suitable for debonding brackets from all of these locations, and the offset feature of the tool tips provides good clearance over the patient's lips during tool rotation. The general concept of the invention is equally useful (with suitable adjustment of tip offset angulation and spacing) on lingual brackets or on other appliances located elsewhere on the teeth. For convenience, the invention has been described in terms of its primary application to orthodontic brackets, but it is our intent that the term "bracket" be broadly construed to include any kind of orthodontic or dental appliance which is cemented to a tooth surface, and which requires eventual debonding and removal.

What is claimed is:

1. A debonding tool for removing an adhesively bonded orthodontic bracket from a tooth, the bracket having a body with opposed noncircular surfaces of known contour and spacing, the tool comprising a central handle portion and a pair of fixed, spaced-apart tips having surfaces with a contour and spacing substantially identical to said known contour and said spacing of said opposed bracket surfaces, said tips extending from the central portion and being separated and contoured to define a slot in which the bracket body can be fitted with the tips in mating engagement with said bracket surfaces so the tool and bracket can be rotated together about an axis generally perpendicular to the tooth surface to break the adhesive bond.

2. The tool defined in claim 1. wherein the central portion is elongated, and terminates in an end portion defining said tips and extending laterally away from a longitudinal axis of the central portion so the tips are offset from the central portion.

3. The tool defined in claim 2 wherein the central portion is elongated and generally rectangular in cross-section, the tool having end portions extending oppositely and laterally away from opposite ends of the central portion, each end portion terminating in said slot-defining tips.

4. The tool defined in claim 3 wherein the slots are of different widths.

5. The tool defined in claim 4 wherein the tool is made of stainless steel, and the tips are hardened to resist abrasion.

6. The tool defined in claim 4 wherein the slots have longitudinal axes which are generally perpendicular to the longitudinal axis of the tool central portion.

7. The tool defined in claim 6 wherein said surfaces of said tips are flat and parallel to form a rectangular slot.

8. The tool defined in claim 1 wherein said surfaces of the slot-defining tips include inwardly extending lands which are spaced apart to fit over and engage a base portion of the opposed bracket surfaces, the remainder of the slot being enlarged to form clearance spaces between the tips and tie-wing portions of the bracket.

9. A debonding tool for removing an adhesively bonded ceramic bracket which is cemented to a tooth, the bracket having substantially flat and parallel spaced-apart mesial and distal sides, the tool comprising an elongated central handgrip portion, and a first end portion extending laterally from the central portion and terminating in a pair of tips having substantially flat and parallel inner facing surfaces which are spaced apart by a distance corresponding to the spacing of the bracket mesial and distal sides, whereby the tool tips can be fitted over the bracket in engagement with the mesial and distal sides to enable bracket debonding by rotary movement of the tool and bracket about an axis generally perpendicular to the tooth surface to which the bracket is secured.

10. The tool defined in claim 9, and further comprising a second end portion extending laterally from the central portion, the end portions being positioned at opposite ends of the central portion, and the second portion having tips corresponding to those in the first portion, but with different tip spacing so the tool defines slots of two different widths.

11. The tool defined in claim 10 wherein the end portions and tips protrude sufficiently laterally from the handle portion to provide lip clearance for the handle portion when the tool is rotated in engagement with the bracket.

12. The tool defined in claim 9 wherein the slot-defining tips have outer ends with inner surfaces defining inwardly extending lands which are spaced apart to fit over and engage a base portion of the opposed bracket surfaces, the remainder of the slot being enlarged to form clearance spaces between the tips and tie-wing portions of the bracket.

13. A process for removing an orthodontic bracket having a base which is adhesively bonded to a tooth surface, comprising the steps of:
   fitting a debonding tool over the bracket so that a pair of fixed, spaced apart tips of the tool are in face-to-face, complemental engagement with opposed surfaces of the bracket; and
   rotating the tool to effect corresponding rotation of the bracket and base about an axis generally perpendicular to the tooth surface to which the bracket is bonded, and thereby fracturing the adhesive bond to release the bracket base from the tooth.

14. The process defined in claim 13 wherein rotation is effected in a quick snap movement.

15. The process defined in claim 13 wherein the bracket is made of a ceramic material, and wherein rotation of the tool and bracket is performed in a quick snap rotary movement around said axis generally perpendicular to said tooth surface.

16. The process defined in claim 13 wherein the bracket has base and tie-wing portions, and the tool is engaged with only the base portion.

* * * * *